(12) United States Patent
Yamamoto et al.

(10) Patent No.: US 7,648,728 B2
(45) Date of Patent: Jan. 19, 2010

(54) METHOD FOR PRODUCING BONE FILTER OF CALCIUM PHOSPHATE

(75) Inventors: Akira Yamamoto, Tokyo (JP); Yusuke Iimori, Tokyo (JP); Yuko Miyazaki, Kanagawa (JP)

(73) Assignee: Hoya Corporation, Tokyo (JP)

( * ) Notice: Subject to any disclaimer, the term of this patent is extended or adjusted under 35 U.S.C. 154(b) by 725 days.

(21) Appl. No.: 11/177,409

(22) Filed: Jul. 11, 2005

(65) Prior Publication Data

US 2006/0013894 A1    Jan. 19, 2006

(30) Foreign Application Priority Data

Jul. 13, 2004    (JP)    ............................. 2004-205961

(51) Int. Cl.
*A61K 6/083*    (2006.01)
(52) U.S. Cl. ...................... 427/2.26; 427/2; 427/376.1; 427/427; 427/34; 427/352; 427/422; 427/423; 128/92; 424/422; 424/424; 424/426; 424/602; 106/35
(58) Field of Classification Search ...................... 427/2, 427/376.1, 427, 34, 352, 422, 423; 424/422, 424/424, 426, 602; 106/35
See application file for complete search history.

(56) References Cited

U.S. PATENT DOCUMENTS

| 4,687,675 A | * | 8/1987 | Nakano et al. | ............. | 427/2.27 |
| 5,030,474 A | * | 7/1991 | Saita et al. | ................. | 427/2.27 |
| 5,320,844 A | * | 6/1994 | Liu | ............................ | 424/422 |

FOREIGN PATENT DOCUMENTS

JP    6-237984    8/1994

OTHER PUBLICATIONS

English Language translation of JP 6-237984, dated Aug. 30, 1994.

* cited by examiner

*Primary Examiner*—Michael Komakov
*Assistant Examiner*—Andrew Bowman
(74) *Attorney, Agent, or Firm*—Greenblum & Bernstein, P.L.C.

(57) ABSTRACT

A method for producing a calcium phosphate bone filler by preparing a mixed liquid comprising a calcium solution and a phosphoric acid solution in such a manner that a substrate of calcium phosphate exists in the mixed liquid, thereby precipitating calcium phosphate on the substrate to form a coating layer, and heat-treating the resultant composite comprising the substrate and the coating layer.

17 Claims, 16 Drawing Sheets

500 nm

2 μm

Amount of Distilled Water Introduced (ml)

—○— Amount of $Ca^{2+}$ Eluted From Sintered HA Particles
—◇— Amount of $Ca^{2+}$ Eluted From Bone Filler of Calcium Phosphate
---●--- Concentration of $Ca^{2+}$ Eluted From Sintered HA Particles
---◆--- Concentration of $Ca^{2+}$ Eluted From Bone Filler of Calcium Phosphate

METHOD FOR PRODUCING BONE FILTER OF CALCIUM PHOSPHATE

FIELD OF THE INVENTION

The present invention relates to a method for producing a bone filler of calcium phosphate having stability and affinity in a living body.

BACKGROUND OF THE INVENTION

Because calcium phosphate compounds are easily absorbed and fixed to human tissues, they are neither rejected by living bodies nor cause necrosis. Accordingly, they are commercially available for artificial bones, artificial teeth, fillers (hereinafter referred to as "bone fillers") in various forms such as sintered bodies, granules, putties, etc.

Most calcium phosphate products are hydroxyapatite ceramics having a chemical formula of $Ca_{10}(PO_4)_6(OH)_2$. The hydroxyapatite ceramics have sufficient strength as bone fillers, accelerating bone regeneration in bone-lost portions. The bone filler of hydroxyapatite embedded in a living body is attached and/or fixed to a living hard tissue. The capability of accelerating bone regeneration in bone-lost portions is called "bone conduction."

Because the embedded bone filler is not fully fixed to a living bone until it is attached and fixed thereto, troubles are likely to occur. Though hydroxyapatite bone fillers have bone conduction, they are not quickly adhered or fixed to a living bone. The attachment or fixing of the hydroxyapatite bone filler to a living bone usually takes 4-5 weeks. Recently, research is vigorously conducted to shorten a time period for attaching and/or fixing the bone filler to a living hard tissue.

As an index of the capability of forming bone in a living body, there is "bone-inducing capability," in addition to the bone conduction. The bone-inducing capability is the capability of forming bone in other portions than bone-lost portions. When a material having the bone-inducing capability is used for a bone filler, the formation of bone is induced even in a gap between the bone filler and a living bone, effective to shorten a time period for the bone filler to be fixed to a living hard tissue.

Tricalcium phosphate (TCP) soluble in a living body is known as a bone-inducing material. Because TCP is more soluble in a living body than hydroxyapatite, it is expected that the TCP embedded in a living body makes the differentiation, induction, etc. of osteoblasts easy. However, a filler made only of TCP cannot exist stably in a living body because it is extremely soluble. The TCP filler is likely to have insufficient strength after a long period of time passes from embedding. Accordingly, it cannot be used as a bone filler for a portion needing mechanical strength. Development has thus been conducted to provide a filler formed by a composite comprising hydroxyapatite stable in a living body and high-solubility TCP.

A bone filler of hydroxyapatite and TCP can be produced, for instance, by arranging TCP powder around a sintered body of hydroxyapatite powder and sintering the resultant composite. The hydroxyapatite powder and the TCP powder used for this method can be produced, for instance, by mixing an aqueous phosphoric acid solution with an aqueous calcium solution. However, which is formed among many crystal systems of calcium phosphate depends on the ratio of phosphoric acid to calcium, the pH of a mixed solution, etc. Accordingly, production conditions change as a synthesis reaction proceeds, failing to obtain homogeneous hydroxyapatite or TCP.

JP6-237984 A discloses an implant material for a living body, which is a calcium phosphate sintered body comprising a hydroxyapatite phase and a tricalcium phosphate phase, with different constituent proportions between an inner crystal layer and an outer crystal layer. It also disclose as methods for producing this implant material, (a) a method of coating or immersing a porous body of calcium phosphate having a calcium/phosphorus (Ca/P) atomic ratio of 1.4-1.75 with or in a calcium phosphate frit or its mixture with hydroxyapatite powder, and sintering it, and (b) a method of coating or immersing the above porous body of calcium phosphate with or in a phosphorus compound or phosphoric acid, and sintering it. These methods can produce implant materials for a living body, whose crystal phases are different in constituent proportions between inner layers and outer layers, the percentage of TCP in the outer layers being relatively high. However, it is difficult to surely form the outer layer with TCP, and to control the thickness of the outer layer, resulting in the production of limited implant materials.

OBJECTS OF THE INVENTION

Accordingly, an object of the present invention is to provide a method for easily producing a bone filler of calcium phosphate having sufficient mechanical strength and bone-inducing capability.

DISCLOSURE OF THE INVENTION

As a result of intensive research in view of the above object, the inventors have found that when an aqueous phosphoric acid solution is slowly added to a mixture of a calcium phosphate substrate and an aqueous calcium solution, calcium phosphate crystals are precipitated on a substrate surface, and that the heat treatment of the resultant composite can provide a bone filler of calcium phosphate comprising a substrate and a coating layer. The present invention has been completed based on this finding.

Thus, the method for producing a bone filler of calcium phosphate according to the present invention comprises preparing a mixed liquid comprising a calcium solution and a phosphoric acid solution with a substrate of calcium phosphate existing therein, thereby precipitating calcium phosphate on the substrate to form a coating layer, and heat-treating the resultant composite comprising the substrate and the coating layer.

The calcium solution and the phosphoric acid solution are mixed preferably such that the coating layer has a smaller Ca/P ratio than that of the substrate. The substrate preferably has a Ca/P ratio of 1.6-1.9. The calcium solution and the phosphoric acid solution are preferably mixed such that the mixed liquid has a Ca/P ratio of 1.0-1.59. It is preferable that the Ca/P ratio continuously decreases from the substrate to the coating layer.

The substrate is preferably made of calcium phosphate, more preferably hydroxyapatite, which is preferably sintered. The substrate may be porous or dense. The substrate may be constituted by particles or a sintered body.

The mixed liquid preferably has a pH of 4-9, a needle-shaped crystal of calcium phosphate is preferably precipitated on the substrate. The heat treatment is carried out at a temperature of 700-1000° C.

BEST MODE FOR CARRIED OUT THE INVENTION

Figure 1:
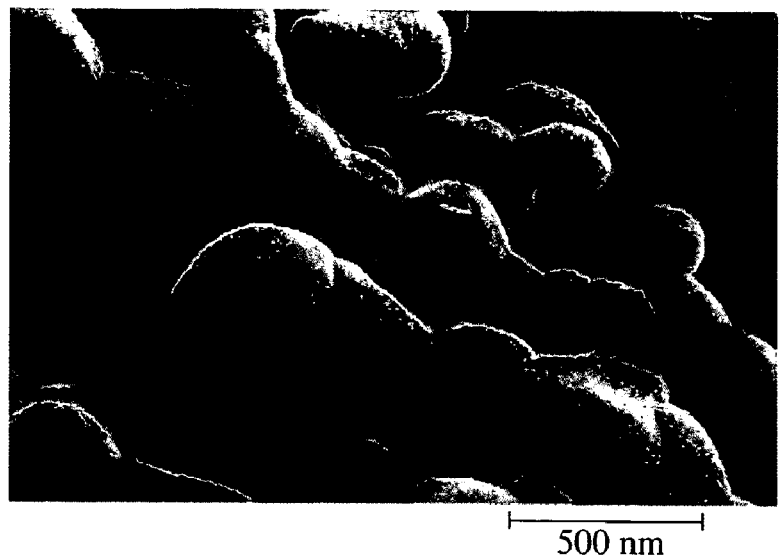
FIG. 1 is a photomicrograph showing sintered HA particles.

[1] Bone Filler of Calcium Phosphate (1) Substrate

The substrate may be fine particles or a sintered body. The fine particles preferably have an average diameter of 1-9000 µm. The sintered body may be in a shape of a cylinder, prisms, a hollow cylinder, cuboids, etc. The substrate may be porous or dense. When the substrate is porous, osteoblasts, etc. so easily enter into the substrate that the calcium phosphate bone filler exhibits large affinity for a living body. When the substrate is dense, the calcium phosphate bone filler has large mechanical strength.

The substrate is made of calcium phosphate having little solubility in a living body. The substrate preferably has a Ca/P ratio of 1.6-1.9. The calcium phosphate having a Ca/P ratio of 1.6-1.9 is stable in a living body because of little solubility. It is preferably hydroxyapatite. The substrate is preferably sintered. In the case of the sintered substrate, a calcium phosphate bone filler can exist stably in a living body for a long period of time.

Fine hydroxyapatite particles and a hydroxyapatite sintered body used for the substrate may be produced by usual methods. It is known that fine particles or a sintered body of hydroxyapatite can be produced from an aqueous phosphoric acid solution and an aqueous calcium solution, and methods for making them porous or dense are also known. Commercially available hydroxyapatite granules and green bodies, and their sintered bodies may be used for the substrate.

(2) Coating Layer

The coating layer is formed on at least part of the substrate surface. When the coating layer is formed on a most part (for instance, 80% or more) of the substrate surface, the calcium phosphate bone filler exhibits large bone-inducing capability. When the substrate is porous, the coating layer is preferably formed even in pores of the substrate. The coating layer is preferably as thick as 1 nm to 15 µm.

The coating layer is made of calcium phosphate having high solubility in a living body. The Ca/P ratio of the coating layer is smaller than that of the substrate. The Ca/P ratio of the coating layer is preferably 1.0-1.59, more preferably 1.45-1.55. The calcium phosphate having a Ca/p ratio of 1.0-1.59 has high solubility in a living body. Accordingly, when the coating layer has a Ca/P ratio of 1.0-1.59, calcium ions are easily eluted from the coating layer in a living body, so that the calcium phosphate bone filler exhibits large affinity for a living body. The coating layer is particularly preferably made of β-TCP. The coating layer of β-TCP is easily dissolved in a living body, exhibiting large bone-inducing capability.

The Ca/P ratio decreases in the bone filler continuously from the substrate to the coating layer. For instance, when the Ca/P ratio of the calcium phosphate bone filler having a hydroxyapatite substrate and a coating layer of β-TCP decreases continuously from the substrate to the coating layer, there is an unclear boundary region between the substrate and the coating layer, in which both hydroxyapatite and β-TCP exist. The boundary region has a larger hydroxyapatite ratio on the substrate side and a larger β-TCP ratio on the coating layer side. The calcium phosphate bone filler having a smoothly changing Ca/P ratio is easily fixed to a living bone. Such calcium phosphate bone filler can be produced by the method of the present invention described below.

[2] Production of Calcium Phosphate Bone Filler (1) Preparation of Aqueous Calcium Solution The aqueous calcium solution preferably has a concentration of 10 mmol/L to 0.5 mol/L. When the calcium concentration is more than 0.5 mol/L, calcium phosphate crystals are not likely to be uniformly precipitated. Calcium salts used for the aqueous calcium solution may be calcium hydroxide, calcium nitrate, etc.

The substrate is in contact with the aqueous calcium solution. For instance, when the substrate is in the form of calcium phosphate particles, the aqueous calcium solution containing the substrate is stirred to form a suspension. When the substrate is a sintered body, the substrate is immersed in the aqueous calcium solution. In any case, to obtain a calcium phosphate bone filler having a coating layer on the entire surface of the substrate, the substrate should be in full contact with the aqueous calcium solution. Taking fine calcium phosphate particles for an example of the substrate, the production of the calcium phosphate bone filler will be explained below.

(2) Formation of Deposited Calcium Phosphate Layer

When an aqueous phosphoric acid solution is slowly added to a suspension comprising an aqueous calcium solution and a substrate, calcium phosphate is precipitated on the substrate surface, to form a composite comprising the substrate and a calcium phosphate layer deposited thereon. It is preferable to drop the aqueous phosphoric acid solution while keeping the suspension uniform by stirring. The aqueous phosphoric acid solution is added, such that the pH of a mixed liquid comprising the aqueous calcium solution, the aqueous phosphoric acid solution and the substrate becomes preferably 4-9, more preferably 5-8. When the pH of the mixed liquid is 4-9, calcium phosphate crystals are precipitated on the substrate surface. When the pH is 4 or more and less than 5, the precipitated calcium phosphate tends to have a brushite crystal structure ($CaHPO_4.2H_2O$). Also, when the pH is 5-9, the precipitated calcium phosphate tends to be hydroxyapatite or its precursor. The deposited layer is preferably composed of needle-shaped, fine particles. When the substrate has a porous structure, the needle-shaped, fine particles tend to be precipitated not only on the surface but also in fine pores.

The concentration and dropping speed of the aqueous phosphoric acid solution dropped are set such that the pH of the resultant mixed liquid is always in a preferred range. The preferred concentration of the aqueous phosphoric acid solution is 10 mmol/L to 0.5 mol/L. When the concentration is more than 0.5 mol/L, phosphoric acid has locally too high concentration in the mixed liquid to form uniform calcium phosphate crystals.

A composite of the substrate and a deposited calcium phosphate layer formed in the suspension can be centrifugally separated out. A centrifugal separation will be explained specifically. The suspension is rotated at about 1000-10000 rpm for about 1-15 minutes, to remove the resultant supernatant liquid. It is preferable to repeat 3 times or more an operation of adding water to the remainder and subjecting the resultant mixture to centrifugal separation to remove a supernatant liquid.

(3) Heat Treatment

The isolated composite is heat-treated. The heat treatment temperature is preferably 700-1000° C. When the heat treatment temperature exceeds 1000° C., a β-TCP phase is likely to be converted to an α-TCP phase. When the heat treatment temperature is lower than 700° C., sufficient crystallization does not occur, failing to easily produce β-TCP. For instance, when the composite is heat-treated at 1000° C., the heat treatment is completed in about 0.5-4 hours.

Even when the deposited calcium phosphate layer is brushite, it is converted to high-solubility calcium phosphate such as β-TCP, etc. by the heat treatment. This change appears to occur, because calcium atoms near the substrate surface are supplied to the deposited layer, thereby increasing the Ca/P ratio of the deposited layer. Because calcium atoms moving from the substrate to the coating layer constitute an extremely small portion of the substrate, the Ca/P ratio in most part of the substrate does not change by the heat treatment. Accordingly, this production method provides a calcium phosphate bone filler having a calcium phosphate coating layer having high solubility in a living body on a surface of a substrate having little solubility in a living body, such as hydroxyapatite, etc., which has a Ca/P ratio continuously decreasing from the substrate to the coating layer.

The present invention will be explained in further detail referring to Examples below without intention of restricting the present invention thereto.

EXAMPLE 1

(1) Production of Sintered Hydroxyapatite Particles (Substrate)

An aqueous solution of a phosphoric acid salt and an aqueous solution of a calcium salt were mixed to form a hydroxyapatite-containing slurry. The hydroxyapatite-containing slurry was dried by a spray-drying apparatus, granulated, and then classified to an average diameter of about 20 μm. The resultant hydroxyapatite particles (hereinafter referred to as "HA particles") were heated at a speed of about 50° C./hour and kept at 1050° C. for 4 hours for sintering in an electric furnace.

(2) Preparation of Sintered HA-calcium Phosphate Composite 1.0 g of the sintered HA particles obtained in the step (1) in Example 1 were mixed with 50 mL of a saturated aqueous calcium hydroxide solution (concentration: 18 mM), and stirred using a magnetic stirrer to obtain a suspension. An aqueous phosphoric acid solution at a concentration of 0.1 M was dropped into this suspension while stirring, until its pH became 5. After a precipitate containing a sintered HA-deposited calcium phosphate composite was formed in a suspension by sufficient reaction of calcium with phosphoric acid, the suspension was subjected to centrifugal separation at 5000 rpm for 5 minutes to remove a supernatant liquid. After an operation of suspending the remainder with distilled water and carrying out centrifugal separation at 5000 rpm for 5 minutes to remove a supernatant liquid was repeated 3 times, the resultant sintered HA-deposited calcium phosphate composite was washed with distilled water.

(3) Heat Treatment

The sintered HA-deposited calcium phosphate composite was heated at 1000° C. for 1 hour to obtain a bone filler of calcium phosphate.

(4) Evaluation

The sintered HA particles, the sintered HA-deposited calcium phosphate composite, and the calcium phosphate bone filler were placed on a sample table for a scanning electron microscope (SEM), and vapor-deposited with an platinum-palladium alloy for surface observation. The observation was carried out by using S-4200 available from Hitachi, Ltd.

FIG. 1 is a photomicrograph of the sintered HA particles used as a substrate. As shown in FIG. 1, the sintered HA particles were porous bodies constituted by primary particles having diameters of about 200-400 nm, which had fine pores of about 20 nm in diameter. The sintered HA particles had smooth surfaces.

Figure 2:
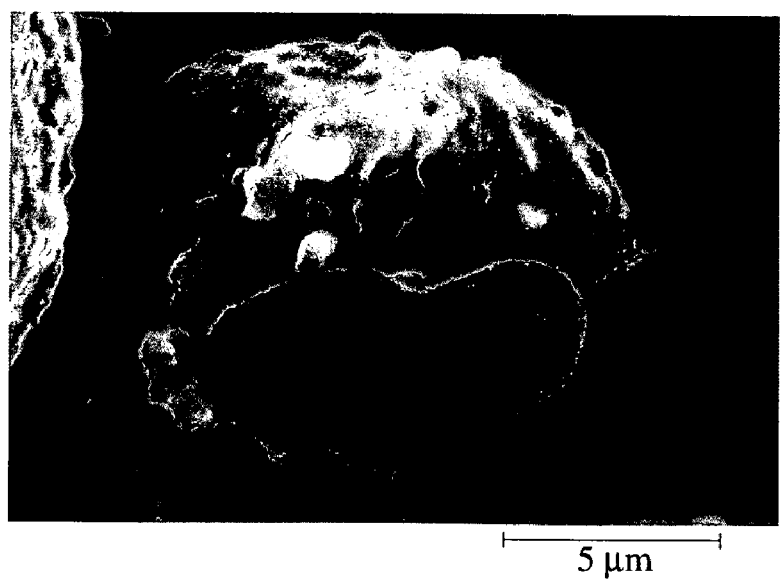
FIG. 2 is a photomicrograph showing a sintered HA-deposited calcium phosphate composite.
Figure 3:
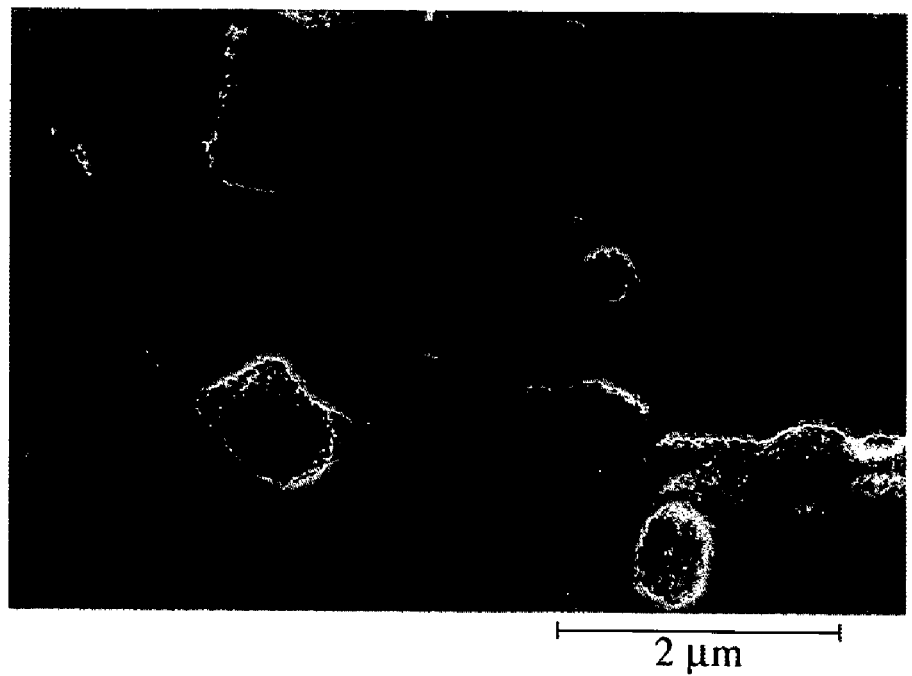
FIG. 3 is a photomicrograph showing the calcium phosphate bone filler of Example 1.

FIG. 2 is a photomicrograph of the sintered HA-deposited calcium phosphate composite. It is clear from FIG. 2 that there were as long flake-shaped precipitates as about 1-10 μm on a surface of each sintered HA particle. FIG. 3 is a photomicrograph of the calcium phosphate bone filler obtained by the heat treatment of the sintered HA-deposited calcium phosphate composite. It is clear from FIG. 3 that the calcium phosphate bone filler had a smooth surface.

Figure 4:
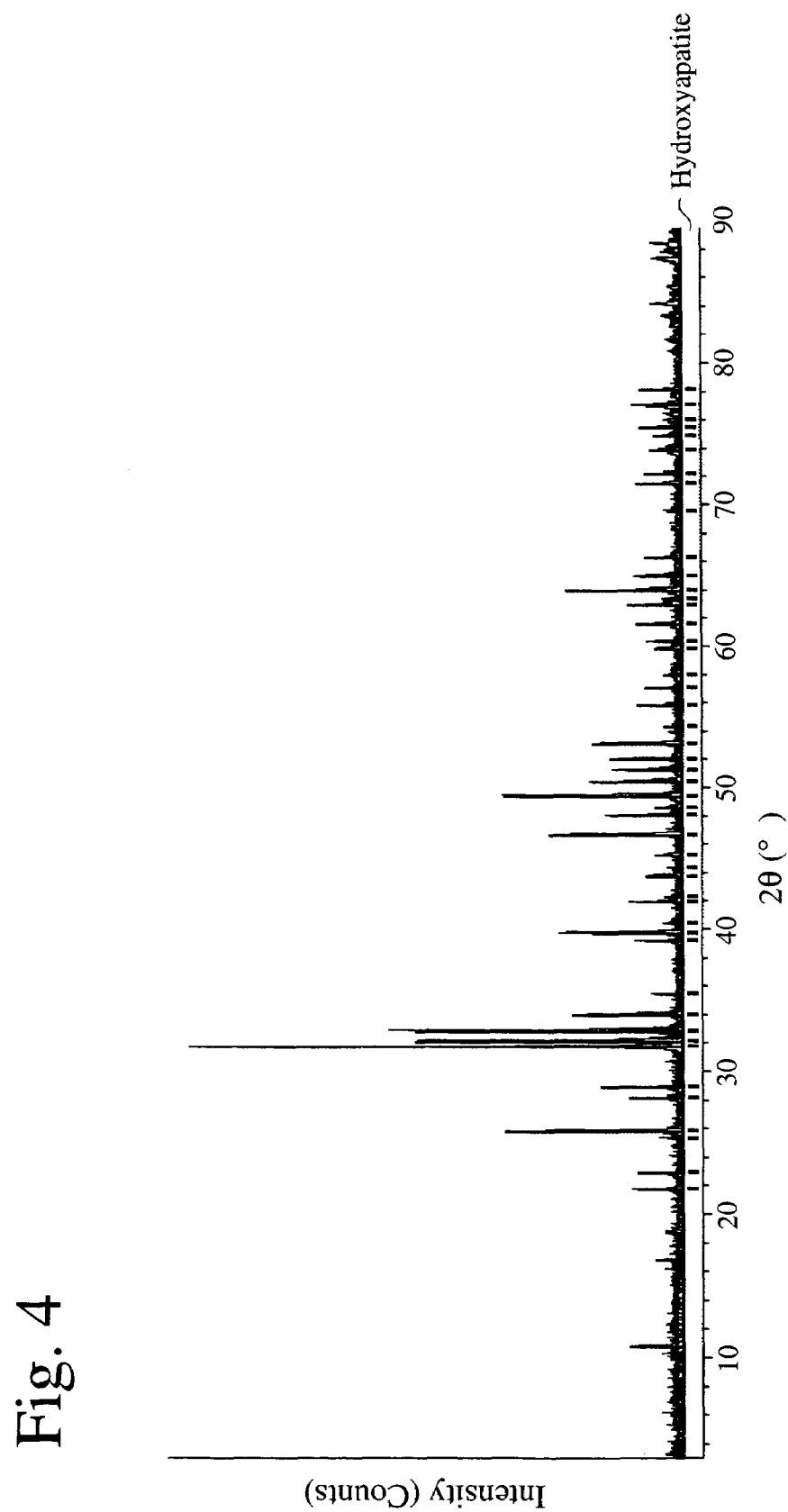
FIG. 4 is a graph showing an X-ray diffraction pattern of sintered HA particles.

Crystal phases in the sintered HA particles, the sintered HA-deposited calcium phosphate composite, and the calcium phosphate bone filler were analyzed by an X-ray diffraction apparatus available from Rigaku Corp. The X-ray diffraction pattern of the sintered HA particles is shown in FIG. 4. It was confirmed that the sintered HA particles had a hydroxyapatite structure. For comparison, an X-ray diffraction pattern typical to hydroxyapatite is shown in Table 1.

TABLE 1

| 2θ | d(Å) | I(f) |
|---|---|---|
| 21.819 | 4.07 | 10 |
| 22.902 | 3.88 | 10 |
| 25.879 | 3.44 | 40 |
| 28.126 | 3.17 | 12 |
| 28.966 | 3.08 | 18 |
| 31.773 | 2.814 | 100 |
| 32.196 | 2.778 | 60 |
| 32.902 | 2.72 | 60 |
| 34.048 | 2.631 | 25 |
| 39.204 | 2.296 | 8 |
| 39.818 | 2.262 | 20 |
| 43.804 | 2.065 | 8 |
| 46.711 | 1.943 | 30 |
| 48.103 | 1.89 | 16 |
| 49.468 | 1.841 | 40 |

Figure 5:
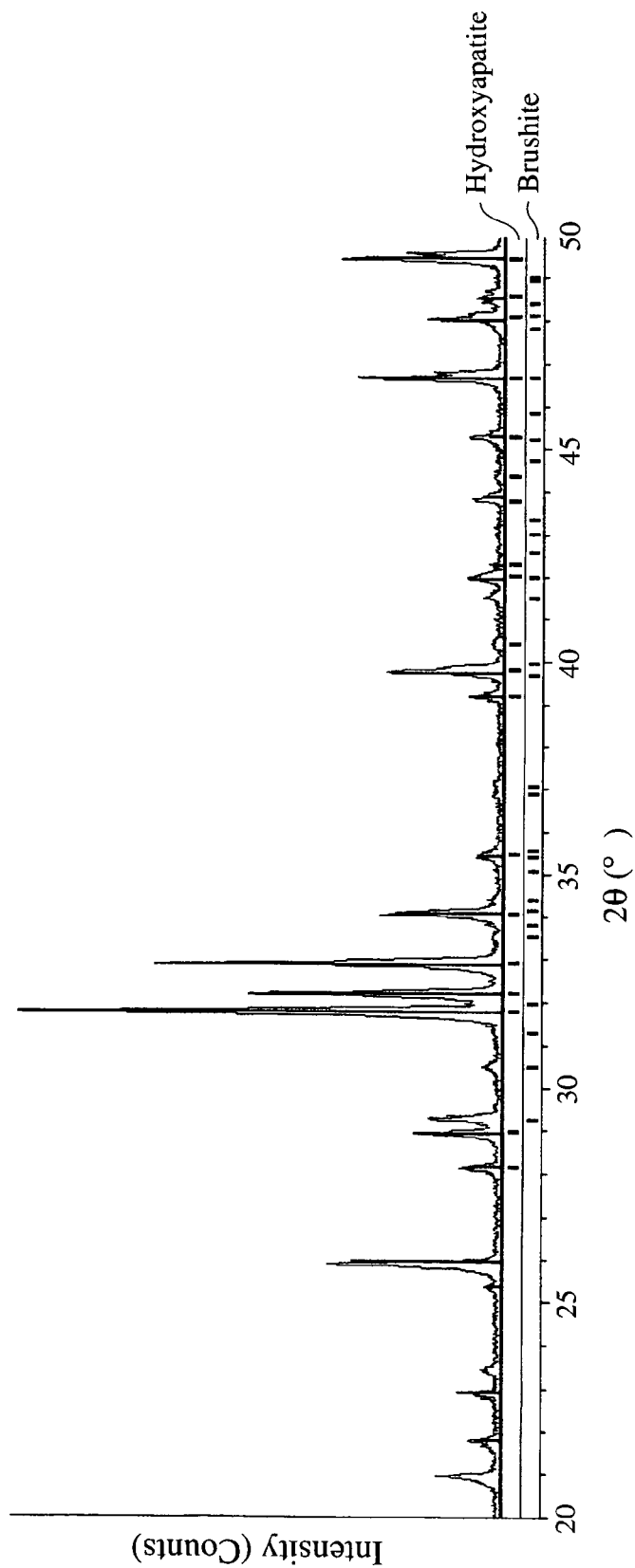
FIG. 5 is a graph showing an X-ray diffraction pattern of a sintered HA-deposited calcium phosphate composite.

FIG. 5 shows an X-ray diffraction pattern of the sintered HA-deposited calcium phosphate composite. Among peaks appearing in the chart of FIG. 5, peaks other than those assigned to a hydroxyapatite substrate appear to be derived from brushite ($CaHPO_4 \cdot 2H_2O$). For comparison, the X-ray diffraction pattern of brushite is shown in Table 2.

TABLE 2

| 2θ | d(Å) | I(f) |
|---|---|---|
| 20.934 | 4.24 | 100 |
| 23.39 | 3.8 | 8 |
| 29.257 | 3.05 | 75 |
| 30.505 | 2.928 | 50 |
| 31.305 | 2.855 | 10 |
| 34.155 | 2.623 | 50 |
| 34.425 | 2.603 | 30 |
| 36.899 | 2.434 | 14 |
| 37.104 | 2.421 | 16 |
| 41.543 | 2.172 | 20 |
| 42.029 | 2.148 | 16 |
| 43.384 | 2.084 | 10 |
| 45.281 | 2.001 | 10 |
| 48.43 | 1.878 | 14 |
| 48.985 | 1.858 | 8 |

Figure 6:
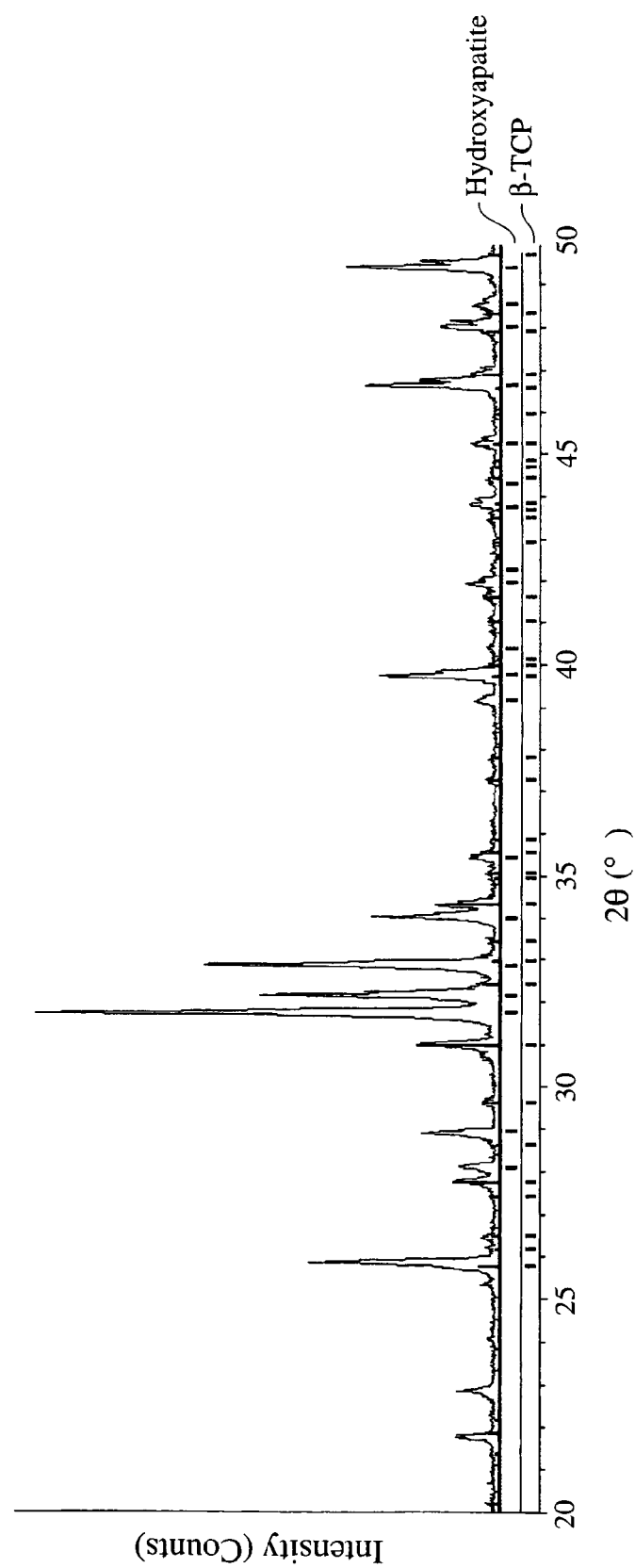
FIG. 6 is a graph showing an X-ray diffraction pattern of the calcium phosphate bone filler of Example 1.

FIG. 6 shows an X-ray diffraction pattern of the bone filler of calcium phosphate. In this X-ray diffraction pattern, there were peaks derived from β-TCP in addition to the peaks of hydroxyapatite. For comparison, the X-ray diffraction pattern of β-TCP is shown in Table 3.

TABLE 3

| 2θ | d(Å) | I(f) |
|---|---|---|
| 21.873 | 4.06 | 16 |
| 25.802 | 3.45 | 25 |
| 27.769 | 3.21 | 55 |
| 29.655 | 3.01 | 16 |
| 31.026 | 2.88 | 100 |
| 32.448 | 2.757 | 20 |
| 34.371 | 2.607 | 65 |
| 35.597 | 2.52 | 12 |
| 41.088 | 2.195 | 14 |
| 41.683 | 2.165 | 12 |
| 46.968 | 1.933 | 20 |
| 47.968 | 1.895 | 16 |
| 48.402 | 1.879 | 14 |
| 49.785 | 1.83 | 12 |

EXAMPLE 2

Figure 7:
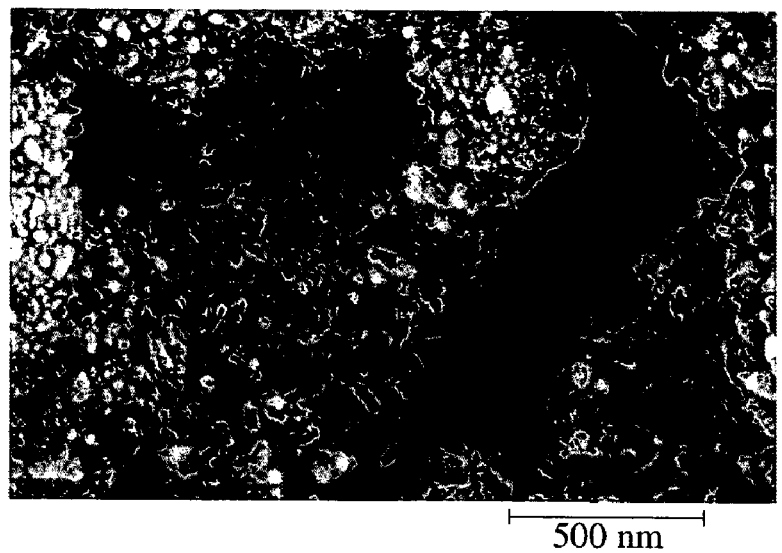
FIG. 7 is a photomicrograph showing another sintered HA-deposited calcium phosphate composite.
Figure 8:
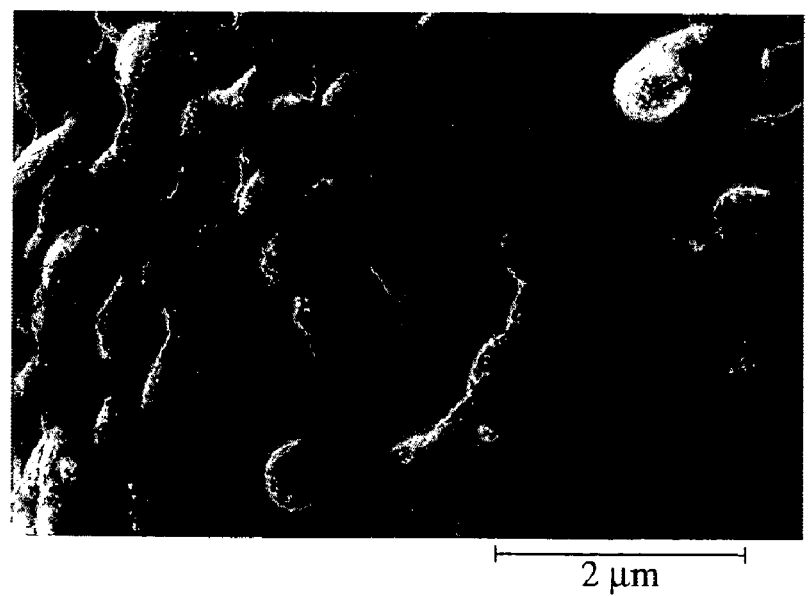
FIG. 8 is a photomicrograph showing the calcium phosphate bone filler of Example 2.
Figure 9:
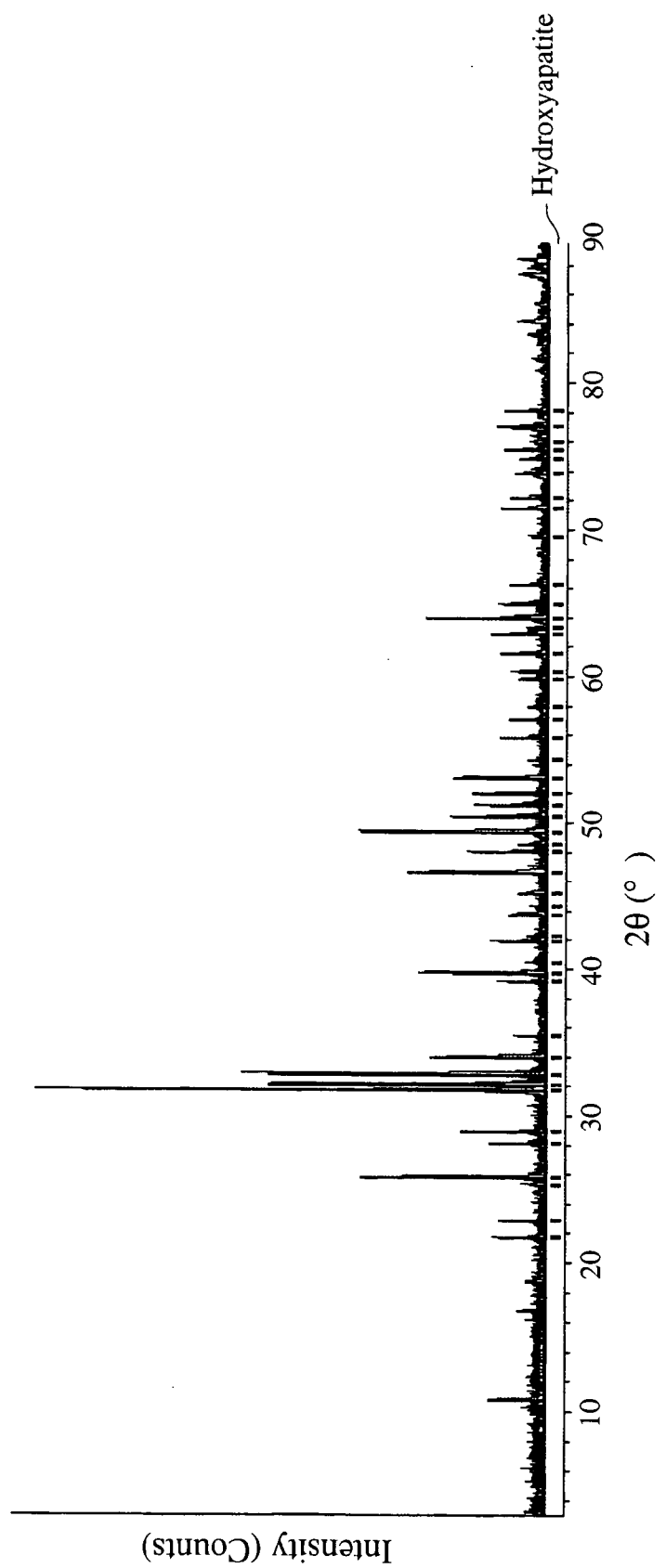
FIG. 9 is a graph showing an X-ray diffraction pattern of sintered HA particles.
Figure 10:
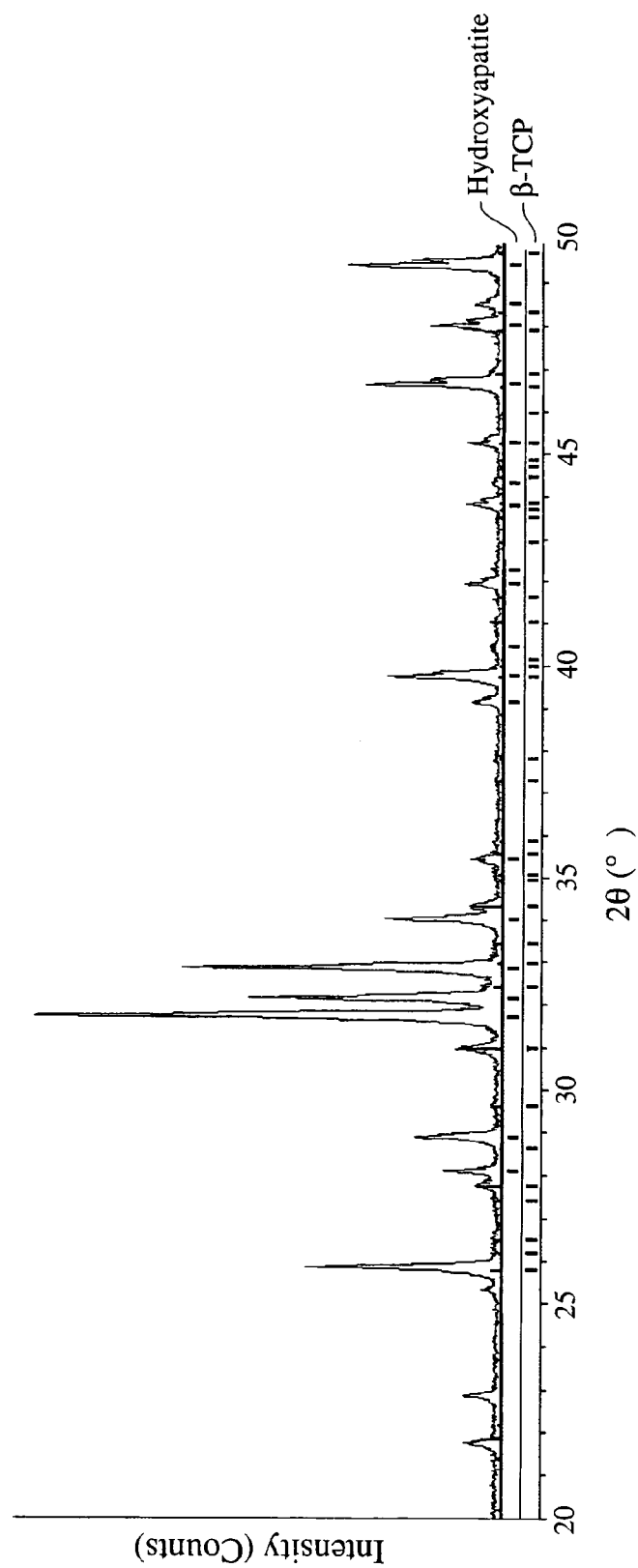
FIG. 10 is a graph showing an X-ray diffraction pattern of the calcium phosphate bone filler of Example 2.

A sintered HA-deposited calcium phosphate composite and a calcium phosphate bone filler were produced in the same manner as in Example 1, except that an aqueous phosphoric acid solution (concentration: 0.1 M) was dropped into a saturated aqueous calcium hydroxide solution to adjust the pH to 8, and subjected to electron microscopic observation and X-ray structure analysis. FIGS. 7 and 8 are the photomicrographs of the sintered HA-deposited calcium phosphate composite and the bone filler of calcium phosphate, and FIGS. 9 and 10 are graphs showing their X-ray diffraction patterns.

As shown in FIG. 7, the sintered HA-deposited calcium phosphate composite had needle-shaped crystals of about 10-200 nm in length precipitated on sintered HA particles as a substrate. The X-ray diffraction pattern shown in FIG. 9 is a typical diffraction pattern of hydroxyapatite, in which the diffraction patterns of other calcium phosphate compounds were not observed.

It is clear from FIG. 8 that the calcium phosphate bone filler was a porous body having a smooth surface. As shown in FIG. 10, the X-ray diffraction pattern of the calcium phosphate bone filler included an X-ray diffraction pattern of β-TCP in addition to that of hydroxyapatite.

EXAMPLE 3

HA particles were produced in the same manner as in the step (1) in Example 1, and formed into a disc having a diameter of 16.25 mm and a thickness of 2.5 mm by a rubber press at 2000 kgf/cm². The disc-shaped HA green body was heated to 1050° C. at a speed of about 50° C./hour and kept at 1050° C. for 4 hours for sintering in an electric furnace.

With the sintered HA disc immersed in a saturated aqueous calcium hydroxide solution, an aqueous phosphoric acid solution was dropped until the pH of the mixed liquid became 8. After the completion of the reaction, a composite of the sintered HA disc and a deposited calcium phosphate layer was taken out of the mixed liquid, washed with distilled water sufficiently, and then dried at 50° C. This sintered HA disc-calcium phosphate composite was heated at 1000° C. for 1 hour to obtain a disc-shaped bone filler of calcium phosphate.

Figure 11:
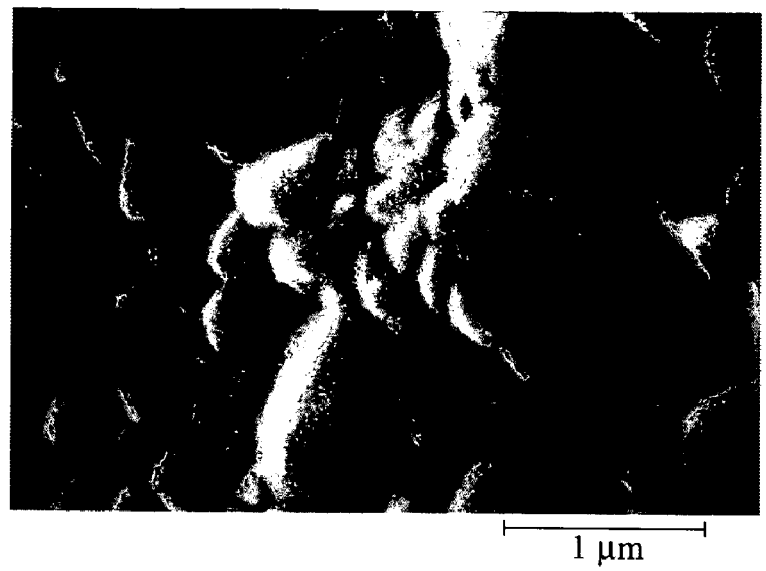
FIG. 11 is an electron photomicrograph showing a sintered HA disc.
Figure 12:
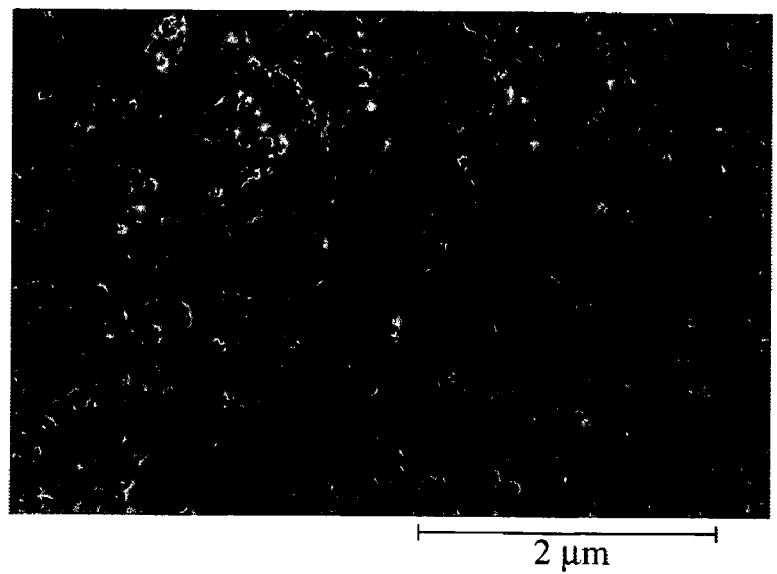
FIG. 12 is an electron photomicrograph showing a sintered HA disc-calcium phosphate composite.
Figure 13:
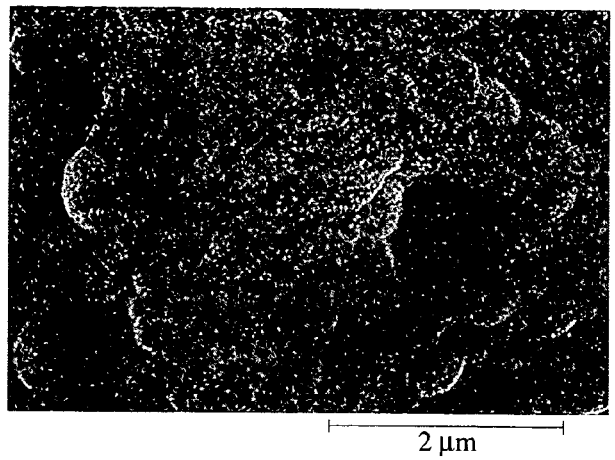
FIG. 13 is an electron photomicrograph showing the calcium phosphate bone filler of Example 3.

The sintered HA disc, the sintered HA disc-calcium phosphate composite and the disc-shaped bone filler of calcium phosphate were subjected to electron microscopic observation. FIG. 11 is an electron photomicrograph of the sintered HA disc. It is clear from FIG. 11 that the sintered HA disc was a smooth-surface, dense body constituted by primary particles of about 500 nm to about several microns in diameter. As shown in FIG. 12, the sintered HA disc-calcium phosphate composite had needle-shaped crystals of about hundreds of nanometers in length on a surface. FIG. 13 is an electron photomicrograph of the bone filler of calcium phosphate. The calcium phosphate bone filler was a dense body having a smooth surface.

EXAMPLE 4

1 g of the sintered HA particles and 1 g of the calcium phosphate bone filler obtained in Example 1 were charged into separate columns each equipped with a filter. Distilled water was introduced at a speed of about 1 mL/minute into each of the column containing the sintered HA particles and the column containing the bone filler of calcium phosphate, to measure the amount and concentration of calcium ions eluted from each column by a calcium ion meter.

Figure 14:
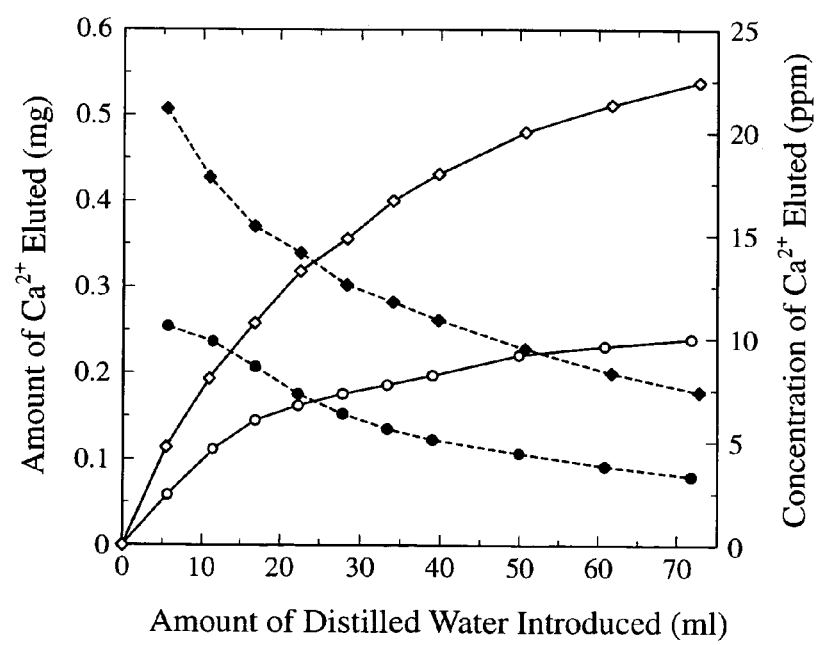
FIG. 14 is a graph showing the amounts and concentrations of calcium ions eluted from the sintered HA particles and the calcium phosphate bone filler obtained in Example 1 when distilled water was introduced thereinto.

FIG. 14 shows the amount and concentration of calcium ions eluted from the sintered HA particles and the bone filler of calcium phosphate. The concentration of eluted calcium ions gradually decreased from the start of elusion in any of the sintered HA particles and the bone filler of calcium phosphate. During measurement, the concentration of calcium ions eluted from the calcium phosphate bone filler was always higher than that from the sintered HA particles.

Comparative Example 1

An aqueous phosphoric acid solution was dropped into a saturated aqueous calcium hydroxide solution in the same manner as in the step (2) in Example 1 except for using no sintered HA particles, to form a precipitate, which was centrifugally separated, washed and dried. The resultant calcium phosphate particles were heated at 1000° C. for 1 hour.

Figure 15:
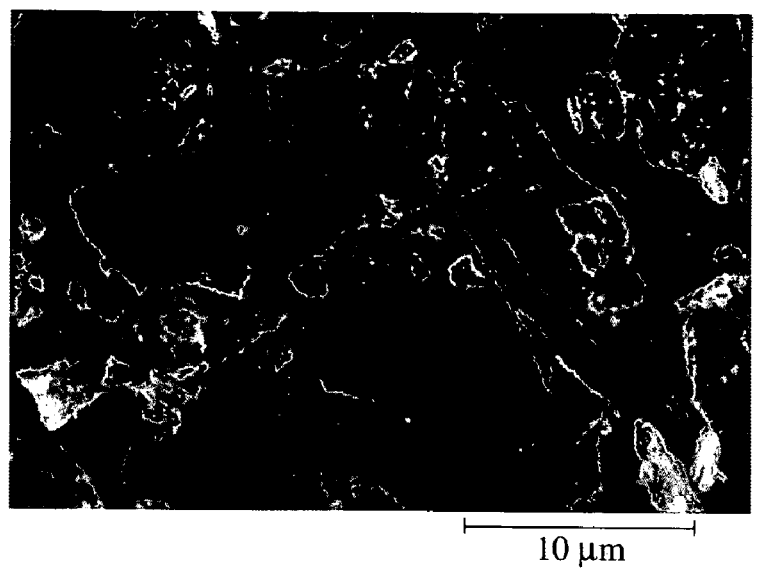
FIG. 15 is an electron photomicrograph showing calcium phosphate particles.
Figure 17:
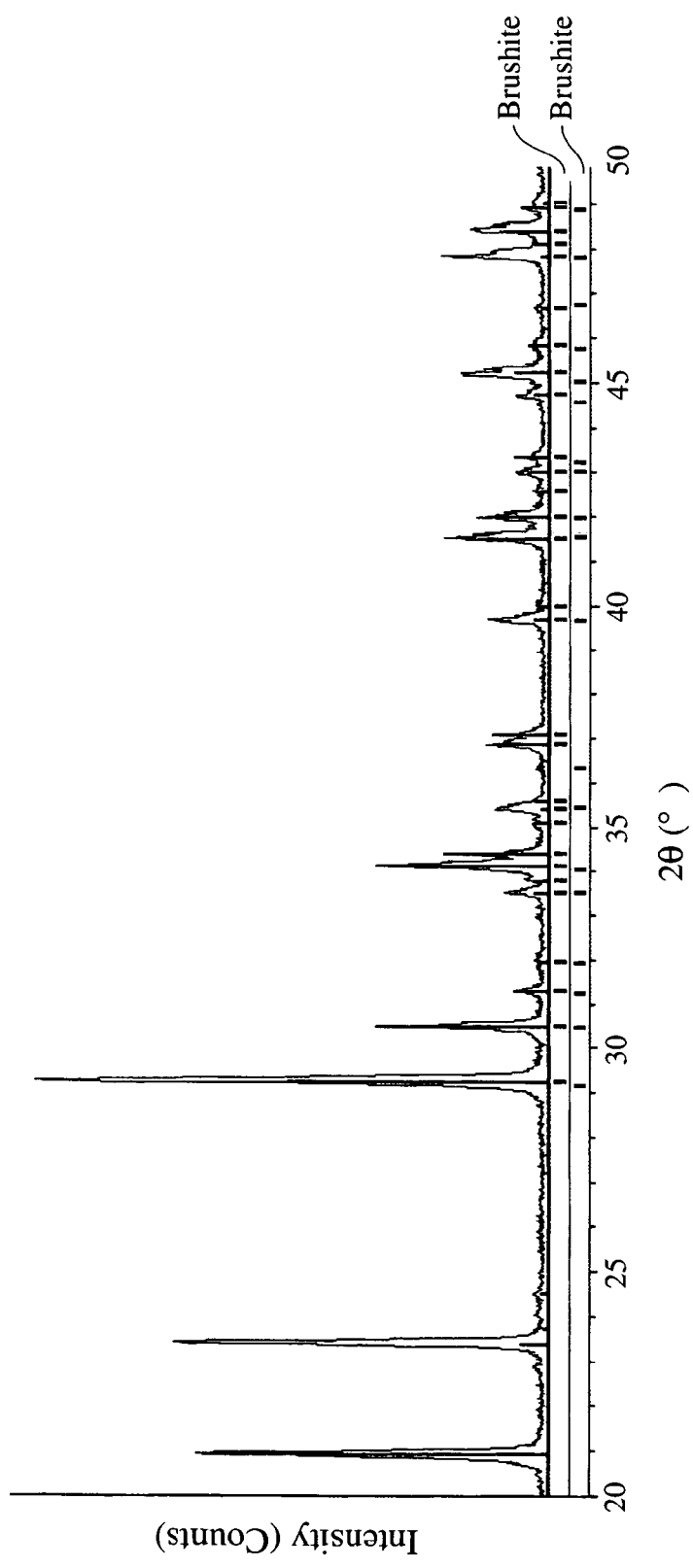
FIG. 17 is a graph showing an X-ray diffraction pattern of calcium phosphate particles.

The calcium phosphate particles before and after sintering were observed by a scanning electron microscope (SEM) and subjected to X-ray structure analysis. As shown in FIG. 15, each calcium phosphate particle had a flake shape as long as about 1-10 μm. FIG. 17 shows an X-ray diffraction pattern of the calcium phosphate particles before sintering. FIG. 17 indicates that the calcium phosphate particles had a crystal form of brushite.

Figure 16:
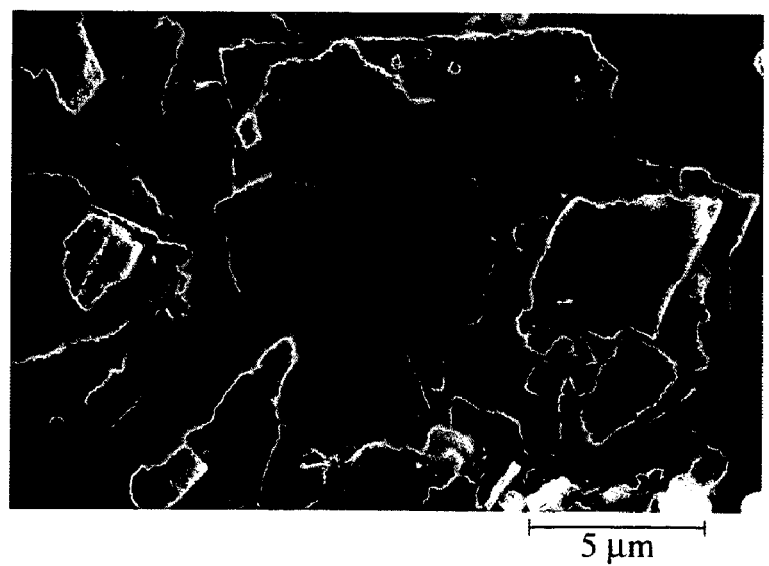
FIG. 16 is an electron photomicrograph showing the sintered calcium phosphate particles of Comparative Example 1.
Figure 18:
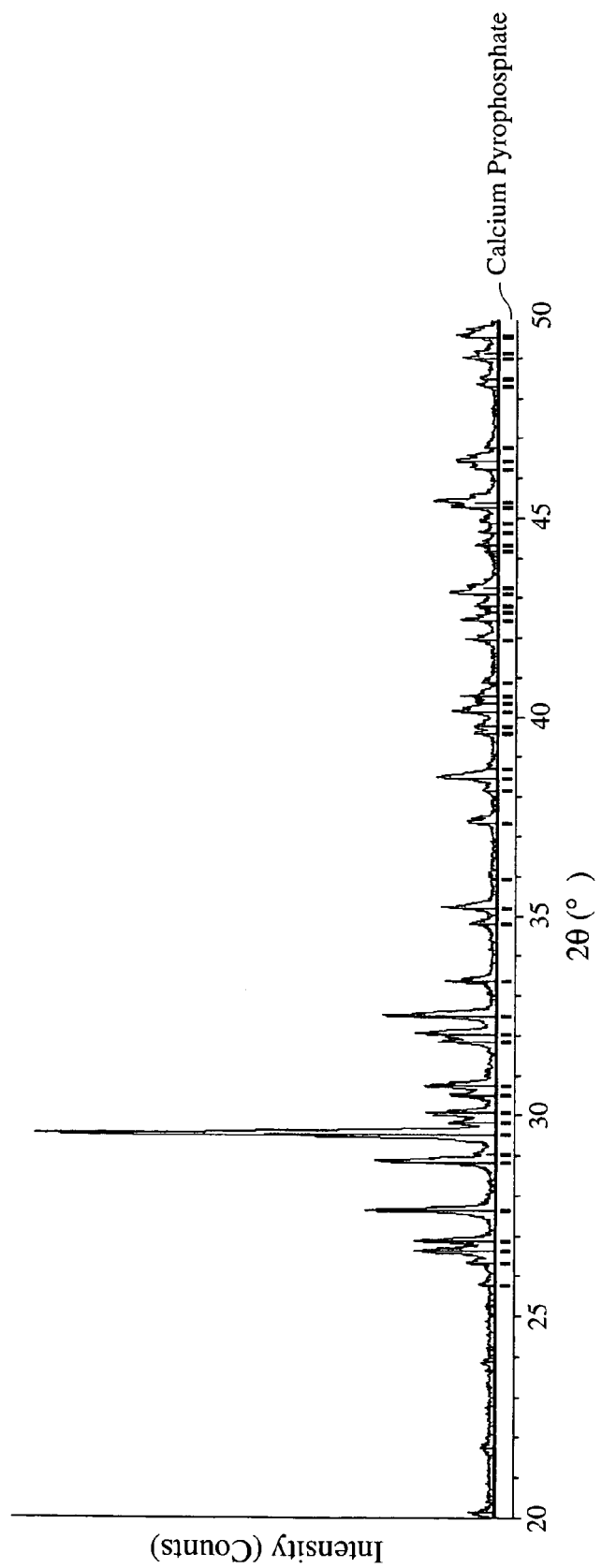
FIG. 18 is a graph showing an X-ray diffraction pattern of the sintered calcium phosphate particles of Comparative Example 1.

As shown in FIG. 16, the sintered calcium phosphate particles were composed of partially sintered thin flakes, whose sides were as long as about one to several tens of microns. FIG. 18 shows an X-ray diffraction pattern of the sintered calcium phosphate particles, which was typical to calcium pyrophosphate (chemical formula: $Ca_2P_2O_7$). For comparison, the X-ray diffraction pattern of calcium pyrophosphate is shown in Table 4.

TABLE 4

| 2θ | d(Å) | I(f) |
|---|---|---|
| 26.667 | 3.34 | 35 |
| 26.914 | 3.31 | 35 |

TABLE 4-continued

| 2θ | d(Å) | I(f) |
|---|---|---|
| 27.681 | 3.22 | 50 |
| 28.87 | 3.09 | 45 |
| 29.554 | 3.02 | 100 |
| 29.868 | 2.989 | 20 |
| 30.105 | 2.966 | 30 |
| 30.537 | 2.925 | 16 |
| 30.774 | 2.903 | 30 |
| 31.878 | 2.805 | 25 |
| 32.077 | 2.788 | 20 |
| 32.545 | 2.749 | 45 |
| 33.407 | 2.68 | 16 |
| 35.264 | 2.543 | 20 |
| 38.524 | 2.335 | 20 |
| 40.208 | 2.241 | 16 |
| 40.605 | 2.22 | 16 |
| 45.353 | 1.998 | 20 |
| 46.509 | 1.951 | 16 |

Reference Example 1

Calcium phosphate particles before and after sintering were produced in the same manner as in Comparative Example 1, except for setting the amount of an aqueous phosphoric acid solution dropped, such that a mixture of the saturated aqueous calcium hydroxide solution and the aqueous phosphoric acid solution had a pH of 8.

Figure 19:
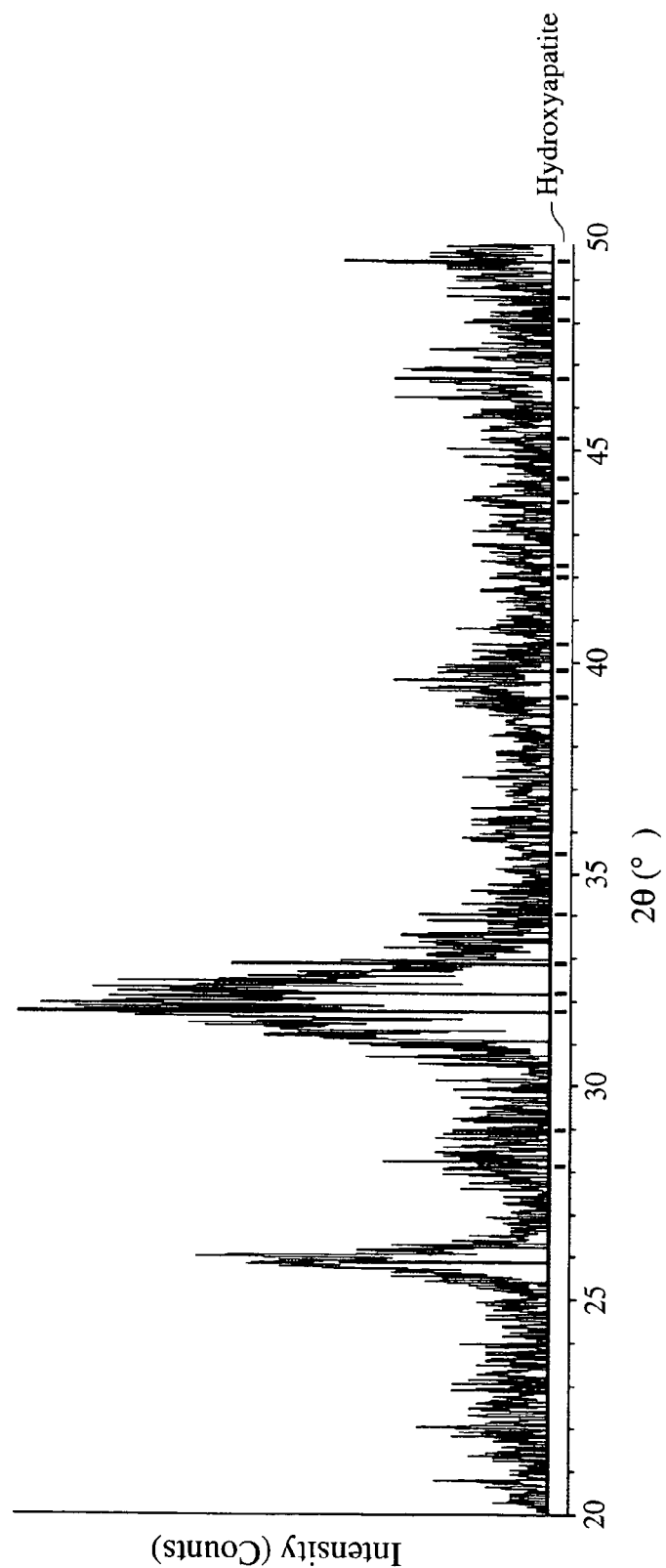
FIG. 19 is a graph showing an X-ray diffraction pattern of calcium phosphate particles.
Figure 20:
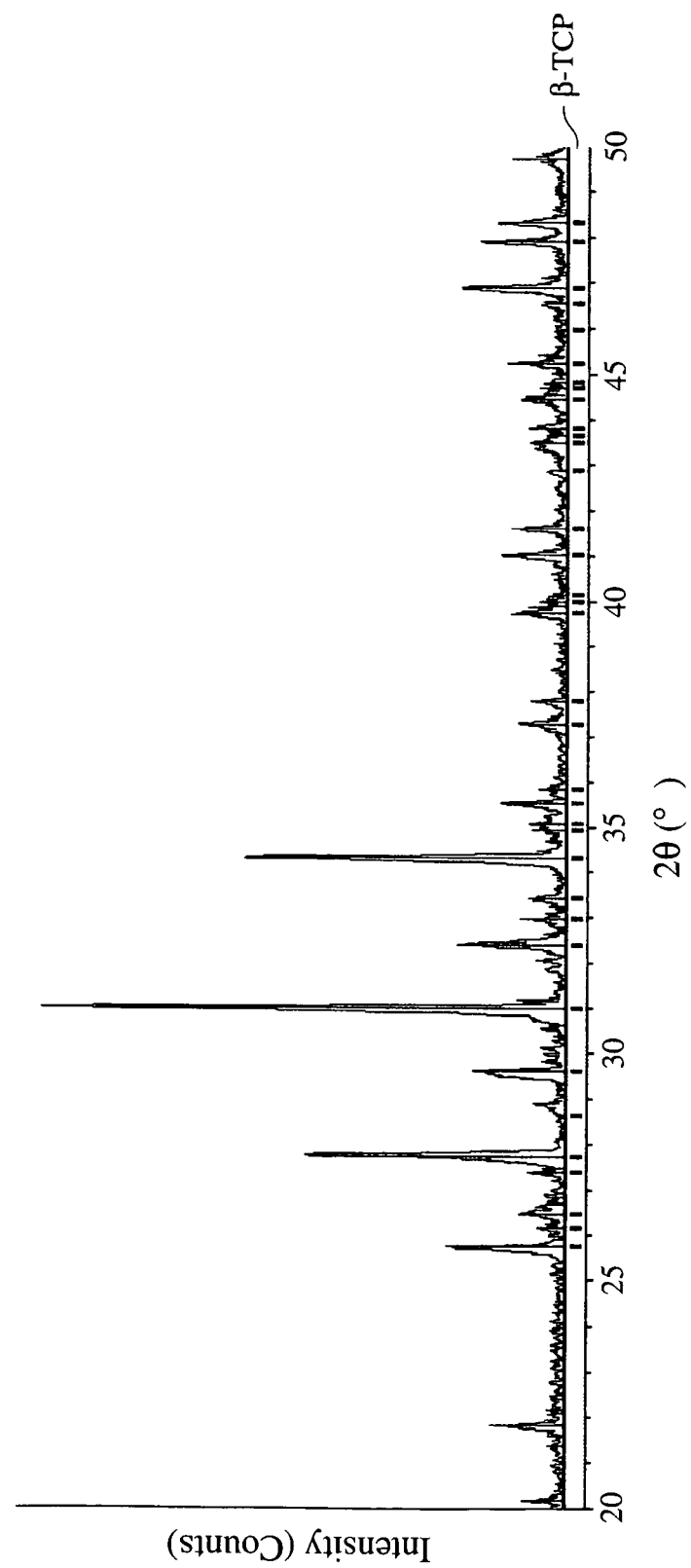
FIG. 20 is a graph showing an X-ray diffraction pattern of the sintered calcium phosphate particles of Comparative Example 1.
Figure 21:
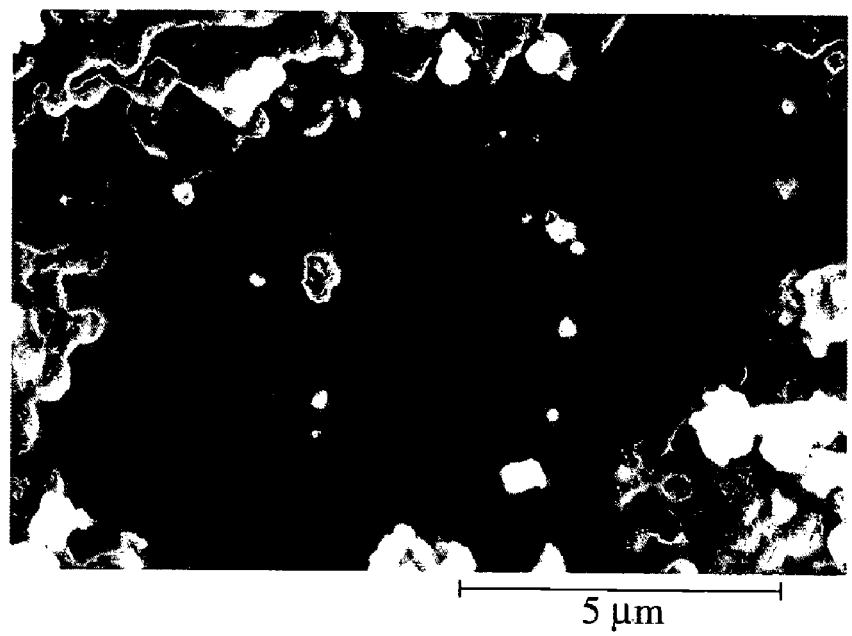
FIG. 21 is a photomicrograph showing the sintered calcium phosphate particles of Comparative Example 1.

FIG. 19 shows an X-ray diffraction pattern of the calcium phosphate particles before sintering, which was typical to an unburned apatite compound. FIG. 20 shows an X-ray diffraction pattern of the sintered calcium phosphate particles. The sintered calcium phosphate particles had a crystal form of β-TCP. As shown in FIG. 21, the sintered calcium phosphate particles were constituted by primary particles of about 500 nm to several microns in diameter, and had smooth surfaces. The evaluation results of Examples 1-3, Comparative Example 1, and Reference Example 1 are shown in Table 5.

TABLE 5

| No. | Production Conditions | | | Crystal Structure | Fine Structure |
|---|---|---|---|---|---|
| | Substrate | pH | Sintering | (XRD) | (SEM) |
| Example 1 | Yes[1] | 5 | Before Sintering | HA[2] + Brushite | Flake-like structure was precipitated on substrate. |
| | | | After Sintering | HA[2] + β-TCP | Porous sintered structure |
| Example 2 | Yes[1] | 8 | Before Sintering | HA[2] | Needle-shaped, fine particles were precipitated. on substrate. |
| | | | After Sintering | HA[2] + β-TCP | Porous sintered structure |
| Example 3 | Yes[3] | 8 | Before Sintering | HA[2] | Needle-shaped, fine particles were precipitated. on substrate. |
| | | | After Sintering | HA[2] + β-TCP | Dense sintered structure |
| Comp. Example 1 | No | 5 | Before Sintering | Brushite | Flake-like structure |
| | | | After Sintering | Calcium Pyrophosphate | Partially sintered flake-like structure |

TABLE 5-continued

| No. | Production Conditions | | | Crystal Structure | Fine Structure |
| --- | --- | --- | --- | --- | --- |
| | Substrate | pH | Sintering | (XRD) | (SEM) |
| Reference Example 1 | No | 8 | Before Sintering | a-HA[(4)] | _[(5)] |
| | | | After Sintering | β-TCP | Porous sintered structure |

Note
[(1)]Sintered hydroxyapatite particles were used as a substrate.
[(2)]HA indicates hydroxyapatite.
[(3)]A sintered hydroxyapatite disc was used as a substrate.
[(4)]a-HA indicates an apatite compound (apatite precursor).
[(5)]Not measured.

The calcium phosphate bone filler of Example 1 was composed of hydroxyapatite and β-TCP, having the same shape as that of the hydroxyapatite substrate. This means that a coating layer of β-TCP was formed on a substrate surface in Example 1. Comparison of the structure before and after sintering revealed that the flake-like structure of brushite was changed to β-TCP by the heat treatment. While brushite had a Ca/P ratio of 1.0, β-TCP had a Ca/P ratio of 1.5, indicating that the heat treatment changed not only the structure but also the Ca/P ratio. The change of the Ca/P ratio appears to be caused by the transfer of calcium atoms from the substrate to the coating layer.

On the other hand, a brushite flake having no substrate was converted to calcium pyrophosphate by the heat treatment (Comparative Example 1). Calcium pyrophosphate has a Ca/P ratio of 1.0 like brushite. In the case of the brushite flake having no substrate, the Ca/P ratio did not change by the heat treatment, thereby forming calcium pyrophosphate having a Ca/P ratio of 1.0 without forming β-TCP having a Ca/P ratio of 1.5.

Because the calcium phosphate bone filler of Examples 2 and 3 had the same shape as that of the substrate, it is presumed that a coating layer of β-TCP was formed on the substrate surface. In any bone fillers of calcium phosphate, a deposited layer made of a calcium-deficient hydroxyapatite was changed to a coating layer of β-TCP by the heat treatment. This structural change was confirmed in Reference Example 1, too. It was confirmed from Examples 2 and 3 that a bone filler having a coating layer of β-TCP could be formed on a substrate surface, when a substrate was constituted not only by hydroxyapatite particles but also by a hydroxyapatite sintered body.

It is thus clear that a calcium phosphate bone filler having a coating layer of β-TCP can be produced even though calcium phosphate having different crystal structures is precipitated on sintered HA particles as a substrate under different conditions such as pH, the shape of the substrate, etc. It was also confirmed that the calcium phosphate bone filler had a large solubility of calcium ions (Example 4), exhibiting large bone-inducing capability in a living body.

EFFECT OF THE INVENTION

According to the method of the present invention, a composite of a substrate and a calcium phosphate layer deposited thereon can be formed without necessitating strict control of a mixing ratio of calcium to phosphoric acid and the pH of a reaction solution, and a coating layer of TCP can be formed on the substrate surface by a subsequent heat treatment, thereby producing a bone filler of calcium phosphate. Such method of chemically precipitating calcium phosphate on the substrate surface is extremely easily carried out, because a calcium phosphate bone filler having a coating layer of TCP can be obtained without synthesizing TCP in advance. Also, because the coating layer can be formed easily regardless of whether the substrate is constituted by fine particles or by a sintered body, calcium phosphate bone fillers having various shapes can be produced. Thus, the method of the present invention for producing a calcium phosphate bone filler is not only extremely easy, but also has large versatility.

The calcium phosphate bone filler produced by the method of the present invention is constituted by a calcium phosphate substrate having little solubility in a living body, and a coating layer having high solubility in a living body because of a smaller Ca/P ratio than that of the substrate, thereby exhibiting bone-inducing capability. Thus, the calcium phosphate bone filler has not only large mechanical strength but also excellent new-bone-forming capability, so that it can be used as a substitute for bones in various portions of the living body.

The present disclosure relates to subject matter contained in Japanese Patent Application No. 2004-205961 filed on Jul. 13, 2004, which is expressly incorporated herein by reference in its entirety.

What is claimed is:

1. A method for producing a bone filler of calcium phosphate, comprising preparing a mixed liquid comprising a calcium solution and a phosphoric acid solution with a substrate of calcium phosphate existing therein, thereby precipitating calcium phosphate on said substrate to form a coating layer, and heat-treating the resultant composite comprising said substrate and said coating layer, wherein said substrate is made of hydroxyapatite.

2. The method for producing a bone filler of calcium phosphate according to claim 1, wherein said coating layer is composed of calcium phosphate having a smaller Ca/P ratio than that of said substrate.

3. The method for producing a bone filler of calcium phosphate according to claim 2, wherein said substrate has a Ca/P ratio of 1.6-1.9.

4. The method for producing a bone filler of calcium phosphate according to claim 3, wherein said calcium solution and said phosphoric acid solution are mixed such that the resultant mixed liquid has a Ca/P ratio of 1.0-1.59.

5. The method for producing a bone filler of calcium phosphate according to claim 1, wherein said substrate is a sintered body of hydroxyapatite.

6. The method for producing a bone filler of calcium phosphate according to claim 1, wherein said mixed liquid has a pH of 4-9.

7. The method for producing a bone filler of calcium phosphate according to claim 1, wherein a needle-shaped crystal of calcium phosphate is precipitated on said substrate.

8. The method for producing a bone filler of calcium phosphate according to claim 1, wherein said heat treatment is carried out at a temperature of 700-1000° C.

9. A method for producing a bone filler of calcium phosphate, comprising:
preparing a mixture of a hydroxyapatite substrate and a calcium salt solution;
adding to the mixture an aqueous phosphoric acid solution, thereby precipitating calcium phosphate on the hydroxyapatite substrate to form a coating layer; and
heat-treating a resultant composite comprising the hydroxyapatite substrate and the coating layer.

10. A method for producing a bone filler of calcium phosphate, comprising preparing a mixed liquid comprising a calcium solution and a phosphoric acid solution with a substrate of calcium phosphate existing therein, thereby precipitating calcium phosphate on said substrate to form a coating layer, and heat-treating the resultant composite comprising said substrate and said coating layer, wherein said substrate comprises pores of about 20 nm diameter.

11. The method for producing a bone filler of calcium phosphate according to claim 10, wherein said coating layer is composed of calcium phosphate having a smaller Ca/P ratio than that of said substrate.

12. The method for producing a bone filler of calcium phosphate according to claim 11, wherein said substrate has a Ca/P ratio of 1.6-1.9.

13. The method for producing a bone filler of calcium phosphate according to claim 12, wherein said calcium solution and said phosphoric acid solution are mixed such that the resultant mixed liquid has a Ca/P ratio of 1.0-1.59.

14. The method for producing a bone filler of calcium phosphate according to claim 10, wherein said substrate is a sintered body of calcium phosphate.

15. The method for producing a bone filler of calcium phosphate according to claim 10, wherein said mixed liquid has a pH of 4-9.

16. The method for producing a bone filler of calcium phosphate according to claim 10, wherein a needle-shaped crystal of calcium phosphate is precipitated on said substrate.

17. The method for producing a bone filler of calcium phosphate according to claim 10, wherein said heat treatment is carried out at a temperature of 700-1000° C.

* * * * *